US009121827B2

(12) United States Patent
Mayer et al.

(10) Patent No.: US 9,121,827 B2
(45) Date of Patent: Sep. 1, 2015

(54) METHOD OF CONTEMPORANEOUSLY MONITORING CHANGES IN ANALYTE CONCENTRATION IN A PLURALITY OF SAMPLES ON INDIVIDUAL SCHEDULES

(75) Inventors: Daniel W. Mayer, Wyoming, MN (US); Timothy A. Ascheman, Elk River, MN (US)

(73) Assignee: Mocon, Inc., Minneapolis, MN (US)

( * ) Notice: Subject to any disclaimer, the term of this patent is extended or adjusted under 35 U.S.C. 154(b) by 680 days.

(21) Appl. No.: 13/173,427

(22) Filed: Jun. 30, 2011

(65) Prior Publication Data

US 2013/0005046 A1 Jan. 3, 2013

(51) Int. Cl.
*G01N 33/02* (2006.01)
*G01N 21/64* (2006.01)
*G01N 21/77* (2006.01)

(52) U.S. Cl.
CPC ........ *G01N 21/6408* (2013.01); *G01N 21/6428* (2013.01); *G01N 21/77* (2013.01); *G01N 2021/6432* (2013.01); *G01N 2021/7786* (2013.01); *Y10T 436/207497* (2015.01)

(58) Field of Classification Search
CPC ........ C12M 1/34; C12M 1/3476; C12Q 1/18; C12Q 1/22; C12Q 2304/40; C12Q 2304/44; C12Q 2304/46; G01N 21/64; G01N 21/6408; G01N 21/6428; G01N 21/77; G01N 21/90; G01N 33/02; G01N 33/04; G01N 33/14; G01N 33/15; G01N 33/18; G01N 33/1866; G01N 33/569; G01N 35/02; G01N 2021/64; G01N 2021/6408; G01N 2021/6432; G01N 2021/7786
USPC ......... 435/29–32, 287.3–287.5, 288.1, 288.7; 436/20–24, 47–48, 62–63, 127, 136, 436/138, 165, 172, 809–810
See application file for complete search history.

(56) References Cited

U.S. PATENT DOCUMENTS

| | | | | |
|---|---|---|---|---|
| 3,067,015 A * | 12/1962 | Lawdermilt | | 422/407 |
| 3,614,434 A * | 10/1971 | Horwitz et al. | | 250/364 |
| 3,773,426 A * | 11/1973 | Mudd | | 356/434 |
| 3,992,631 A * | 11/1976 | Harte | | 250/365 |
| 4,003,709 A * | 1/1977 | Eaton et al. | | 422/86 |
| 4,220,715 A * | 9/1980 | Ahnell | | 435/34 |
| 4,250,266 A * | 2/1981 | Wade | | 422/64 |
| 4,314,029 A * | 2/1982 | Ohtake et al. | | 435/287.5 |
| 4,476,870 A | 10/1984 | Peterson et al. | | |
| 4,810,655 A | 3/1989 | Khalil et al. | | |
| 4,868,110 A * | 9/1989 | DesRosier et al. | | 435/34 |
| 4,907,443 A * | 3/1990 | Pailler | | 73/52 |
| 4,945,060 A * | 7/1990 | Turner et al. | | 435/288.7 |
| 4,947,850 A | 8/1990 | Vanderkooi et al. | | |
| 5,094,955 A * | 3/1992 | Calandra et al. | | 435/288.7 |
| 5,096,813 A * | 3/1992 | Krumhar et al. | | 435/28 |
| 5,155,019 A * | 10/1992 | Sussman et al. | | 435/34 |
| 5,162,229 A * | 11/1992 | Thorpe et al. | | 435/288.7 |
| 5,164,796 A * | 11/1992 | Di Guiseppi et al. | | 356/445 |
| 5,190,729 A | 3/1993 | Hauenstein et al. | | |
| 5,232,839 A * | 8/1993 | Eden et al. | | 435/39 |
| 5,310,658 A * | 5/1994 | Berndt | | 435/34 |
| 5,371,016 A | 12/1994 | Berndt | | |
| 5,372,784 A * | 12/1994 | Morris et al. | | 435/287.9 |
| 5,382,163 A | 1/1995 | Putnam | | |
| 5,387,865 A | 2/1995 | Jerosch-Herold et al. | | |
| 5,407,829 A | 4/1995 | Wolfbeis et al. | | |
| 5,432,061 A * | 7/1995 | Berndt et al. | | 435/34 |
| 5,473,437 A * | 12/1995 | Blumenfeld et al. | | 356/417 |
| 5,498,543 A * | 3/1996 | Berndt | | 435/286.1 |
| 5,516,692 A * | 5/1996 | Berndt | | 435/286.7 |
| 5,518,923 A * | 5/1996 | Berndt et al. | | 435/287.3 |
| 5,595,708 A | 1/1997 | Berndt | | |
| 5,646,049 A * | 7/1997 | Tayi | | 436/518 |
| 5,675,155 A | 10/1997 | Pentoney, Jr. et al. | | |
| 5,695,640 A | 12/1997 | Tseng | | |
| 5,718,842 A | 2/1998 | Papkovsky et al. | | |
| 5,795,773 A * | 8/1998 | Read et al. | | 435/287.5 |
| 5,858,769 A * | 1/1999 | DiGuiseppi et al. | | 435/287.3 |
| 5,863,752 A * | 1/1999 | Court et al. | | 435/34 |
| 5,888,825 A * | 3/1999 | Carr et al. | | 436/48 |
| 6,025,189 A * | 2/2000 | Bolea et al. | | 435/287.4 |
| 6,074,607 A | 6/2000 | Slovacek et al. | | |
| 6,144,448 A | 11/2000 | Mitoma | | |
| 6,153,701 A | 11/2000 | Potnis et al. | | |
| 6,165,741 A | 12/2000 | Wilson et al. | | |
| 6,266,211 B1 | 7/2001 | Thomas, III et al. | | |
| 6,362,175 B1 | 3/2002 | Vinogradov et al. | | |

(Continued)

FOREIGN PATENT DOCUMENTS

| | | |
|---|---|---|
| EP | 0705897 A1 | 4/1996 |
| WO | 2007120637 A2 | 10/2007 |
| WO | 2010066273 A1 | 6/2010 |
| WO | 2010132741 A2 | 11/2010 |
| WO | 2010132746 A2 | 11/2010 |
| WO | 2010132749 A2 | 11/2010 |
| WO | 2010132780 A2 | 11/2010 |
| WO | 2010132823 A2 | 11/2010 |
| WO | 2010132829 A2 | 11/2010 |
| WO | 2010143172 A1 | 12/2010 |
| WO | 2011091811 A1 | 8/2011 |

OTHER PUBLICATIONS

Austin, Ead et al., "Opto-electronic systems for addressing Ru oxygen sensors: their design optimization and calibration process", Invited Paper, Optoelectronics Research Centre, University of Southampton, Southampton S017 IBJ.

(Continued)

*Primary Examiner* — Arlen Soderquist
(74) *Attorney, Agent, or Firm* — Sherrill Law Offices, PLLC

(57) ABSTRACT

A method of contemporaneously monitoring changes in analyte concentration in a plurality of samples using a single monitoring device, wherein monitoring can be commenced and continued on independent timelines for each sample.

22 Claims, 1 Drawing Sheet

(56) References Cited

U.S. PATENT DOCUMENTS

| | | |
|---|---|---|
| 6,379,969 B1 | 4/2002 | Mauze et al. |
| 6,395,555 B1 | 5/2002 | Wilson et al. |
| 6,689,438 B2 | 2/2004 | Kennedy et al. |
| 6,777,479 B1 | 8/2004 | Bernard et al. |
| 7,138,270 B2 | 11/2006 | Papkovsky et al. |
| 7,368,153 B2 | 5/2008 | Barmore et al. |
| 7,427,501 B2 * | 9/2008 | Bachur et al. ............... 435/287.3 |
| 7,534,615 B2 | 5/2009 | Havens |
| 7,569,395 B2 | 8/2009 | Havens et al. |
| 7,618,591 B2 | 11/2009 | Slowey |
| 7,674,626 B2 | 3/2010 | Papkovsky et al. |
| 7,785,894 B2 * | 8/2010 | Smolander et al. ........... 436/166 |
| 8,557,539 B2 * | 10/2013 | Eden et al. ........................ 435/40 |
| 2003/0032171 A1 * | 2/2003 | Gemmell et al. ........... 435/286.2 |
| 2003/0050543 A1 | 3/2003 | Hartmann |
| 2003/0062262 A1 | 4/2003 | Mansouri et al. |
| 2005/0159497 A1 | 7/2005 | Gauthier et al. |
| 2006/0002822 A1 | 1/2006 | Papkovsky et al. |
| 2007/0041011 A1 | 2/2007 | Hayden et al. |
| 2007/0042412 A1 | 2/2007 | Papkovsky et al. |
| 2007/0160500 A1 * | 7/2007 | Baumfalk et al. ........... 422/82.07 |
| 2007/0212789 A1 | 9/2007 | Havens et al. |
| 2007/0212792 A1 | 9/2007 | Havens et al. |
| 2008/0051646 A1 | 2/2008 | Papkovsky et al. |
| 2008/0117418 A1 | 5/2008 | Claps et al. |
| 2008/0146460 A1 | 6/2008 | Pollok et al. |
| 2008/0148817 A1 | 6/2008 | Miller et al. |
| 2008/0190172 A1 | 8/2008 | Jones |
| 2008/0199360 A1 | 8/2008 | Shahriari |
| 2008/0215254 A1 | 9/2008 | Leiner et al. |
| 2008/0242870 A1 | 10/2008 | Meador et al. |
| 2009/0028756 A1 | 1/2009 | Shahriari |
| 2009/0029402 A1 | 1/2009 | Papkovsky |
| 2009/0130700 A1 | 5/2009 | Ince et al. |
| 2009/0142796 A1 * | 6/2009 | Yu et al. ........................... 435/32 |
| 2010/0116017 A1 | 5/2010 | Mayer et al. |
| 2010/0209693 A1 | 8/2010 | Hester et al. |
| 2010/0291619 A1 | 11/2010 | Robinson et al. |
| 2011/0136163 A1 | 6/2011 | Papkovsky et al. |
| 2011/0136247 A1 | 6/2011 | Papkovsky et al. |

OTHER PUBLICATIONS

De Francisci, M. et al., "Real-Time Estimation of Oxygen Concentration in Micro-Nemo-Vessels", Proceedings of the 26th Annual International Conference of the IEEE EMBS San Francisco, CA, USA' Sep. 1-5, 2004.

Eaton, K. et al., "Effect of Humidity on the Response Characteristics of Luminescent PtOEP Thin Film Optical Oxygen Sensors", Sensors & Actuators, Elsevier Science B. V., vol. 82, pp. 94-104, 2002.

Technical Manual, "Freudenberg Grafted Products", Sep. 2006, pp. 1-32.

Papkovsky, D. et al., "Phosphorescent Sensor Approach for Non-Destructive Measurements of Oxygen in Packaged Foods: Optimization of Disposable Oxygen Sensors and Their Characterization Over a Wide Temperature Range", Department of Biochemistry National University of Ireland, Analytical Letters, 33 (9), pp. 1755-1777, 2000.

Poenninger A. et al., "Determination of the Coefficient of Moisture Expansion (CME)", Proceedings of the 9th International Symposium on Materials in a Space Environment Noordwijk, The Netherlands, Jun. 16-20, 2003; pp. 567-572.

Ashley et al., "Wetting-Dewetting Transition Line in Thin Polymer Films", Research Article, ACS Publications, Sep. 9, 2005, pp. 9518-9523.

O'Mahony et al., "Analysis of Total Aerobic Viable Counts in Samples of Raw Meat Using Fluorescence-Based Probe and Oxygen Consumption Assay", Elsevier, Food Control, Science Control, 2008, pp. 1-7.

O'Mahony et al., "Rapid High-Throughput Assessment of Aerobic Bacteria in Complex Samples by Fluorescence-Based Oxygen Respirometry". American Society for Microbiology, Feb. 2006, vol. 72 No. 2, pp. 1279-1287.

* cited by examiner

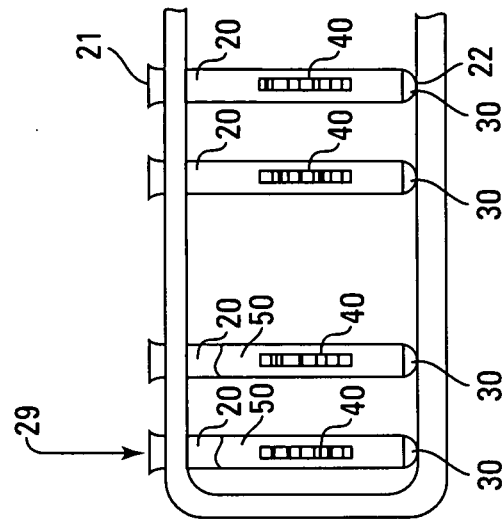
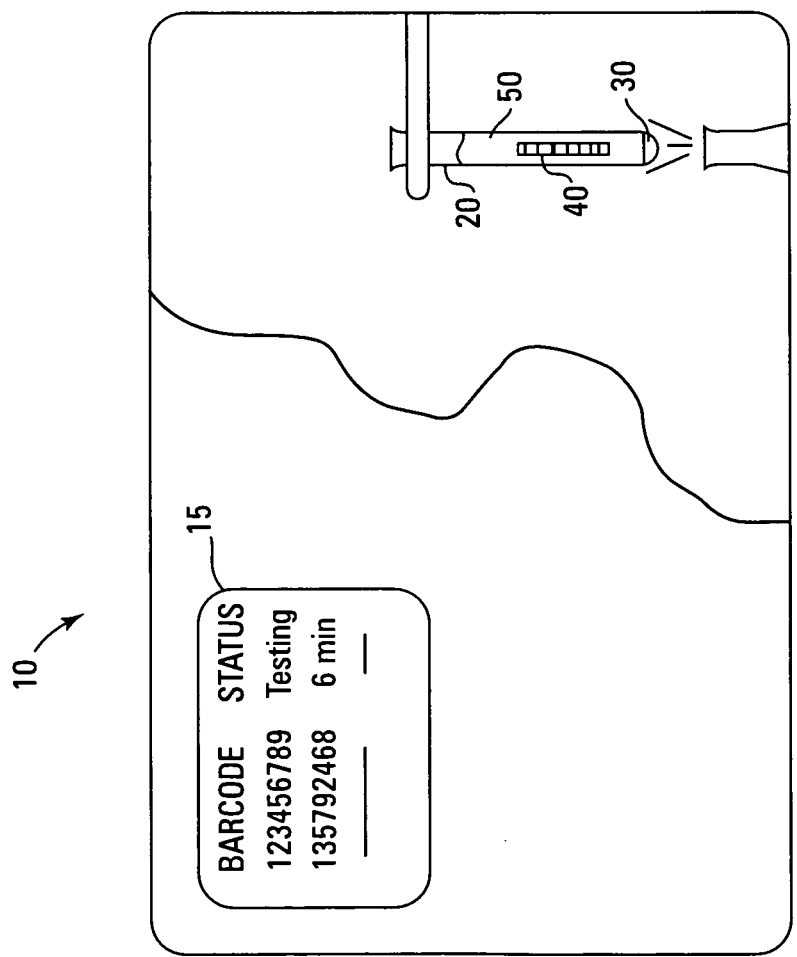

METHOD OF CONTEMPORANEOUSLY MONITORING CHANGES IN ANALYTE CONCENTRATION IN A PLURALITY OF SAMPLES ON INDIVIDUAL SCHEDULES

BACKGROUND

Photoluminescent sensors or probes are a widely employed method of measuring analyte concentration, typically oxygen, within an enclosed space such as a package or container. See, for example United States Published Patent Applications 2009/0029402, 2008/8242870, 2008/215254, 2008/199360, 2008/190172, 2008/148817, 2008/146460, 2008/117418, 2008/0051646, and 2006/0002822, and U.S. Pat. Nos. 7,569,395, 7,534,615, 7,368,153, 7,138,270, 6,689,438, 5,718,842, 4,810,655, and 4,476,870.

Briefly, analyte concentration within a package or container can be measured by placing an analyte sensitive photoluminescent probe within the package or container, allowing the probe to equilibrate within the package or container, exciting the probe with radiant energy, and measuring the extent to which radiant energy emitted by the excited probe is quenched by the presence of the target analyte. Such optical sensors are available from a number of suppliers, including Presence Precision Sensing, GmbH of Regensburg, Germany, Oxysense of Dallas, Tex., United States, and Luxcel Biosciences, Ltd of Cork, Ireland.

Such probes can be used to quantify a rate of oxygen uptake by biological and chemical samples, thereby serving as a biomarker of cell or organism viability. Also, many oxygen-dependent enzymatic and chemical reactions can be monitored via oxygen consumption, providing a means for evaluating the performance of various reactants, catalysts, enzymes, etc. and the effect of various conditions (e.g., temperature, pressure, concentrations, etc.).

The placement of photoluminescent probes into vials for monitoring oxygen consumption by a sample placed into the vial is known. U.S. Pat. Nos. 5,371,016 and 6,080,574 describe optical systems for measuring sample sterility and microbial growth by monitoring oxygen consumption by a sample placed within a vial having a fluorescence-based oxygen sensor built into the vial. WO98/15645 describes an optical system that uses a solid-state luminescence-based oxygen sensor to assess a biological sample containing living microorganisms by measuring gradients of dissolved oxygen within the sample. U.S. Pat. No. 5,882,922 describes a system for measuring oxygen consumption in samples using wells containing a solid-state oxygen sensor coating applied to the bottom of each well or soluble oxygen probes added to each sample.

While effective for accurately quantifying a rate of change in analyte concentration within a sample (e.g., oxygen uptake by biological and chemical samples) and thereby allowing quantification of viable microbes within a sample or quantification of a chemical reaction, the systems and techniques employing such technology are time consuming, often creating a choke-point in the distribution of products, such as foodstuffs, from a production facility into the stream of commerce.

Accordingly, a substantial need exists for quick, simple and inexpensive technique for hastening quantification of viable microbes within a sample or quantification of a chemical reaction employing photoluminescent probes that does not sacrifice accuracy or reliability.

SUMMARY OF THE INVENTION

The invention is directed to a method of contemporaneously monitoring changes in analyte concentration in a plurality of samples using a single monitoring device, wherein monitoring can be commenced and continued on independent timelines for each sample. The method includes the steps of (i) obtaining at least two separate and independent vessels, each defining a single retention chamber and having an analyte sensitive probe within the retention chamber, (ii) placing a test sample into each vessel to form filled vessels, and (iii) periodically interrogating the probe within each filled vessel employing a single interrogation device wherein (A) interrogations measure changes in the probe reflective of changes in analyte concentration within the retention chamber of the filled vessel, (B) an initial interrogation is taken at time $t_0$ for each filled vessel, (C) subsequent interrogations of each filled vessel are taken periodically on a schedule measured from the $t_0$ for each filled vessel, and (D) the initial interrogation of each filled vessel is taken at a different time of day.

BRIEF DESCRIPTION OF THE DRAWING

FIG. 1 is a schematic depiction of one embodiment of a system capable of use in practicing the claimed invention.

DETAILED DESCRIPTION OF A PREFERRED EMBODIMENT

Nomenclature

10 Interrogation Device
15 Display Component of Interrogation Device
20 Vessel, Vial or Cuvette
20$n$ $n^{th}$ Vessel, Vial or Cuvette
21 Open Top End of Vessel, Vial or Cuvette
22 Closed Bottom End of Vessel, Vial or Cuvette
29 Retention Chamber of Vessel, Vial or Cuvette
30 Probe
30$n$ Probe in $n^{th}$ Vessel, Vial or Cuvette
40 Barcode
40$n$ Barcode on $n^{th}$ Vessel, Vial or Cuvette
50 Sample
50$n$ Sample in $n^{th}$ Vessel, Vial or Cuvette Construction The invention is directed to a method of contemporaneously monitoring changes in analyte concentration, in a plurality of samples 50 using a single monitoring device 10.

The target analyte can be any molecule of interest capable of being detected (e.g., oxygen $O_2$, carbon dioxide $CO_2$, carbon monoxide CO, etc.). Since the most frequent target-analyte is oxygen, the balance of the disclosure shall be based upon oxygen as the target-analyte without intending to be limited thereby.

The source of the samples 50 is essentially unlimited, including solids, gels, liquids and gases taken from any of a variety of sources such as a processing line (e.g., a food processing line) or a point source (e.g., water tower, sewage treatment system, stream, etc.). Persons of routine skill in the art are capable of selecting and preparing suitable samples 20 for use in the present invention.

Each sample 50 is placed within the retention chamber 29 of a vessel 20 having an open top end 21, a closed bottom end 22, and a probe 30 within the retention chamber 29. The vessel 20 is preferably a vial or cuvette having a high aspect ratio of depth to circumference, such as disclosed in United States Patent Application Publication 2009/0029402, which disclosure is incorporated herein by reference. Since a preferred vessel 20 is a vial or cuvette 20, the balance of the disclosure shall reference the vessel 20 as a vial 20 without intending to be limited thereby.

Each vial 20 is given a unique identification tag 40 such as a barcode or RFID tag.

The preferred methods and compositions described herein are based on the quenching of photoluminescence by an analyte, typically oxygen ($O_2$). Luminescence encompasses both fluorescence and phosphorescence. Electromagnetic radiation in the ultraviolet or visible region is used to excite molecules to higher electronic energy levels. The excited molecules lose their excess energy by one of several methods. One of those methods is fluorescence. Fluorescence refers to the radiative transition of electrons from the first excited singlet state to the singlet ground state ($S_1$ to $S_0$). The lifetime of fluorescence is relatively short, approximately $10^{-9}$ to $10^{-7}$ seconds. However, intersystem crossing from the lowest excited singlet state to the triplet state often occurs and is attributed to the crossing of the potential energy curves of the two states. The triplet state so produced may return to the ground state by a radiative process known as phosphorescence. Phosphorescence is the radiative relaxation of an electron from the lowest excited triplet state to the singlet ground state ($T_1$ to $S_0$). Because the transition that leads to phosphorescence involves a change in spin multiplicity, it has a low probability and hence a relatively long lifetime of $10^{-4}$ to 10 seconds. Fluorescent and phosphorescent lifetime is known to change in a defined fashion relative to changes in the partial pressure of an analyte ($P_A$) capable of quenching the photoluminescent molecules. Hence, the $P_A$ in fluid communication with a photoluminescent material can be determined by measuring photoluminescence lifetime.

In a preferred embodiment, the probes 30 are optically-active, target-analyte partial pressure sensitive materials configured and arranged to experience changes in target-analyte partial pressure $P_A$ in a sample 50 placed within the retention chamber 29 of a vial 20. The analyte-sensitive material is preferably a photoluminescent dye embedded within an analyte permeable polymer matrix. Since the preferred type of probe 30 is an optically-active, target-analyte partial pressure sensitive material, and the most frequent target-analyte of interest is oxygen, the balance of the disclosure shall be based upon a photoluminescent oxygen quenched probe 30 without intending to be limited thereby.

The oxygen-sensitive photoluminescent dye may be selected from any of the well-known oxygen sensitive photoluminescent dyes. One of routine skill in the art is capable of selecting a suitable dye based upon the intended use of the probe. A nonexhaustive list of suitable oxygen sensitive photoluminescent dyes includes specifically, but not exclusively, ruthenium(II)-bipyridyl and ruthenium(II)-diphenylphenanothroline complexes, porphyrin-ketones such as platinum(II)-octaethylporphine-ketone, platinum(II)-porphyrin such as platinum(II)-tetrakis(pentafluorophenyl)porphine, palladium(II)-porphyrin such as palladium(II)-tetrakis(pentafluorophenyl)porphine, phosphorescent metallocomplexes of tetrabenzoporphyrins, chlorins, azaporphyrins, and long-decay luminescent complexes of iridium (III) or osmium(II).

Typically, the hydrophobic oxygen-sensitive photoluminescent dye is compounded with a suitable oxygen-permeable and hydrophobic carrier matrix. Again, one of routine skill in the art is capable of selecting a suitable oxygen-permeable hydrophobic carrier matrix based upon the intended use of the probe and the selected dye. A nonexhaustive list of suitable polymers for use as the oxygen-permeable hydrophobic carrier matrix includes specifically, but not exclusively, polystryrene, polycarbonate, polysulfone, polyvinyl chloride and some co-polymers.

When the probe 30 is based on the quenching of photoluminescence by an analyte, the vial 20, or at least that portion of the vial 20 coated with the probe 30, must allow radiation at the excitation and emission wavelengths to be transmitted to and received from the probe 30 with minimal interference.

Instruments 10 for interrogating probes 30 based on the quenching of photoluminescence by an analyte are well known and commercially available from various sources, including Becton Dickinson of Franklin Lakes, N.J. and Mocon, Inc. of Minneapolis, Minn.

Manufacture of Probe 30 Containing Vials 20

The probe 30 containing vials 20 can be conveniently manufactured by (A) preparing a coating cocktail (not shown) which contains the photoluminescent oxygen-sensitive dye and the oxygen-permeable polymer in an organic solvent (not shown) such as ethylacetate, (B) depositing the cocktail into the bottom 22 of the retention chamber 29, such as by using a syringe (not shown), and (C) allowing the cocktail (not shown) to dry, whereby a solid-state coating is formed within the retention chamber 29 at the bottom 22 of the vial 20, thereby forming a probe 30 within the vial 20.

Generally, the concentration of the polymer in the organic solvent should be in the range of 0.1 to 20% w/w, with the ratio of dye to polymer in the range of 1:20 to 1:10,000 w/w, preferably 1:50 to 1:5,000 w/w.

Use

The probe 30 can be used to quickly, easily, accurately and reliably monitor changes in oxygen concentration within a sample 50 deposited into the retention chamber 29 of the vessel 20 in accordance with traditional methods employed to interrogate such probes 30. Briefly, the probe 30 is used to measure oxygen concentration within a sample 20 deposited into the retention chamber 29 of the vessel 20 by (A) depositing a sample 50 to be tested into the retention chamber 29, and (B) ascertaining the oxygen concentration within the retention chamber 29 by (i) repeatedly exposing the probe 30 to excitation radiation over time, (ii) measuring radiation emitted by the excited probe 30 after at least some of the exposures, (iii) measuring passage of time during the repeated excitation exposures and emission measurements, and (iv) converting at least some of the measured emissions to an oxygen concentration based upon a known conversion algorithm, and (C) reporting at least one of (i) at least two ascertained oxygen concentrations and the time interval between those reported concentrations, and (ii) a rate of change in oxygen concentration within the enclosed space calculated from data obtained in step (B). Conversion algorithms used to convert the measured emissions to an oxygen concentration are well know to and readily developable by those with routine skill in the art.

The radiation emitted by the excited probe 30 can be measured in terms of intensity and/or lifetime (rate of decay, phase shift or anisotropy), with measurement of lifetime generally preferred as a more accurate and reliable measurement technique when seeking to establish oxygen concentration via measurement of the extent to which the dye has been quenched by oxygen.

Testing of individual samples 50 from amongst a plurality of samples $50_n$ can be commenced without delay and continued on separate and discrete schedules for each sample 50 using a single monitoring device 10 by (i) obtaining a first sample $50_1$, (ii) placing the first sample $50_1$ into a vial 20 to form a first sample-containing vial $20_1$, (iii) performing an initial interrogation of the first sample-containing vial $20_1$ with the single interrogation device 10, (iv) performing subsequent interrogations of the first sample-containing vial $20_1$ with the single interrogation device 10 on a schedule measured from the time at which the initial interrogation of the first sample-containing vial $20_1$ was performed, and (v) repeating steps (i) through (iv) for subsequently obtained samples $50_n$ with the initial interrogation of each vial $20_n$ containing a subsequently obtained sample $50_n$ taken whenever each vial $20_n$ is ready for an initial interrogation and the single interrogation device 10 is available—without regard to the time at which the initial interrogation of any other sample-containing vial $20_n$ was taken.

EXAMPLES

Example 1

Prophetic

Manual

Samples of a processed food product are taken from a processing line every hour on the half hour to ascertain viable bacterial count (TVC, APC or CFU) just prior to packaging. Each sample is transported from the processing line to a testing room, digested for a predefined period of time, and deposited into a barcoded vial containing a photoluminescent oxygen-sensitive probe.

Each sample is placed into an instrument capable of reading the barcode on each vial, interrogating the probe in each vial, and for each vial maintaining a database of the results of each interrogation and the time at which each interrogation was taken. The instrument reads the barcode on each inserted vial using a barcode reader. If the vial has not been previously interrogated, the instrument requests the operator to input the lot number of the sample deposited into the vial. Upon receipt of the requested data, the instrument interrogates the probe to obtain an initial reading. The results of the initial reading and the time of day at which the initial reading is taken are recorded and correlated to the barcode of the tested vial. Upon completion of the initial interrogation, a schedule is established for subsequent interrogations of the vial and an operator is instructed to remove the vial from the instrument and place the vial into an incubation chamber.

The instrument displays a chronologically ordered sequence of scheduled interrogations that includes an identification of the vials to be interrogated and an indication of the time remaining until the next scheduled interrogation for each vial. The instrument provides both a visual and audible cue (e.g., ♫ and an accompanying tone) to an operator when an identified vial is to be removed from the incubation chamber and inserted into the instrument for testing. An exemplary display is provided below.

Upon insertion of a vial for a subsequent interrogation, the instrument reads the barcode to ensure that the inserted vial matches the vial scheduled for interrogation, interrogates the vial when the scheduled interrogation time is reached, and signals the operator to remove the vial upon completion of the interrogation. If a vial is inserted after its scheduled interrogation time, the vial is interrogated as quickly as possible after insertion into the instrument.

The results of each interrogation and elapsed time since the initial interrogation for the vial are recorded by the instrument.

Each vial is interrogated until a threshold value is reached in the readings from the probe, at which time the instrument indicates that testing is complete and provides the operator with an indication of whether the sample contained an ACCEPTABLE or UNACEPTABLE viable bacterial count based upon a preestablished threshold. Upon request, the operator can obtain the actual value of the viable bacterial count from the instrument.

Example 2

Prophetic

Automated

Samples of a processed food product are taken from a processing line every hour on the half hour to ascertain viable bacterial count (TVC, APC or CFU) just prior to packaging. Each sample is transported from the processing line to a testing room, digested for a predefined period of time, and deposited into a barcoded vial containing a photoluminescent oxygen-sensitive probe.

Each sample is placed into a carousel capable of holding a plurality of vials. The carousel is housed within an instrument capable of reading the barcode on each vial in the carousel, interrogating the probe in each vial, and for each vial maintaining a database of the results of each interrogation and the time at which each interrogation was taken. A "check status" signal is transmitted to the instrument each and every time the carousel is accessed by an operator. Upon receiving the "check status" signal, the instrument reads the barcode on all vials in the carousel. If the instrument encounters a vial that has not been previously interrogated, the instrument requests the operator to input the lot number of the sample deposited into the vial. Upon receipt of the requested data, the instrument interrogates the probe to obtain an initial reading. The results of the initial reading and the time of day at which the initial reading is taken are recorded and correlated to the barcode of the tested vial. Upon completion of the initial interrogation, a schedule is established for subsequent interrogations of the vial.

The instrument displays a chronologically ordered sequence of scheduled interrogations that includes an identification of the vials to be interrogated and an indication of the time remaining until the next scheduled interrogation for each vial. The instrument automatically locates and interrogates the vials in accordance with the programmed and displayed schedule.

The results of each interrogation and elapsed time since the initial interrogation for the vial are recorded by the instrument.

Each vial is interrogated until a threshold value is reached in the readings from the probe, at which time the instrument indicates that testing is complete and provides the operator with an indication of whether the sample contained an ACCEPTABLE or UNACEPTABLE viable bacterial count based upon a preestablished threshold. Upon request, the operator can obtain the actual value of the viable bacterial count from the instrument.

We claim:

1. A method of monitoring changes in analyte concentration in a plurality of samples, comprising the steps of:
   (a) obtaining at least two separate and independent vessels, each defining a single retention chamber and having an analyte sensitive probe within the retention chamber,
   (b) placing a test sample into each vessel to form filled vessels, and
   (c) periodically interrogating the probe within each filled vessel employing a single interrogation device wherein (i) interrogations measure changes in the probe reflective of changes in analyte concentration within the retention chamber of the filled vessel, (ii) an initial interrogation is taken at time $t_0$ for each filled vessel, (iii) subsequent interrogations of each filled vessel are taken periodically on a schedule measured from the $t_0$ for each filled vessel, and (iv) the initial interrogation of each filled vessel is taken at a different time of day.

2. The method of claim 1, wherein the analyte is oxygen.

3. The method of claim 1, wherein the method monitors consumption of oxygen by viable bacteria in the sample and correlates measured changes in oxygen concentration to a concentration of bacteria in the sample prior to monitoring.

4. The method of claim 1, wherein the vessel is a vial formed from an oxygen barrier material.

5. The method of claim 4, wherein (i) the vials have an open top end and a closed bottom end, and (ii) the probe is positioned within the retention chamber of each vial proximate the bottom end.

6. The method of claim 1, wherein the vessel is a cuvette formed from an oxygen barrier material.

7. The method of claim 1, wherein the step of obtaining at least two separate and independent vessels comprises the step of obtaining at least ten vessels.

8. The method of claim 1, wherein at least two filled vessel are contemporaneously interrogated.

9. The method of claim 8, wherein the initial interrogation for at least one filled vessel occurs subsequent to the subsequent interrogation of at least one other filled vessel.

10. The method of claim 1, wherein at least three filled vessel are contemporaneously interrogated.

11. The method of claim 10, wherein the initial interrogation for at least one filled vessel occurs subsequent to the subsequent interrogation of at least two other filled vessels.

12. The method of claim 10, wherein the initial interrogation for at least two filled vessels occurs subsequent to the subsequent interrogation of at least one other filled vessel.

13. The method of claim 1, wherein at least ten filled vessel are contemporaneously interrogated.

14. The method of claim 1, wherein the probe is an oxygen sensitive photoluminescent dye.

15. The method of claim 14 wherein the oxygen sensitive photoluminescent dye is an oxygen sensitive transition metal complex.

16. The method of claim 15 wherein the oxygen sensitive transition metal complex is selected from the group consisting of a ruthenium bipyridyl, a ruthenium diphenylphenanotroline, a platinum porphyrin, a palladium porphyrin, a phosphorescent complex of a tetrabenzoporphyrin, a chlorin, a porphyrin-ketone, an aza-porphyrin and a long-decay luminescent complex of iridium(III) or osmium(II).

17. The method of claim 1 wherein the test sample is a food product intended for human consumption.

18. The method of claim 1 wherein the food product has been stomached prior to placement in the vessel.

19. The method of claim 1 wherein the interrogations measure changes in the probe reflective of changes in analyte concentration dissolved within the test sample retained within the retention chamber of the filled vessel.

20. The method of claim 1 wherein interrogations measure photoluminescence lifetime.

21. The method of claim 1 wherein a human perceptible reminder signal and information identifying a specific filled vessel scheduled for the next forthcoming subsequent interrogation is generated by the interrogation device for each subsequent interrogation.

22. The method of claim 1 wherein each vessel is tagged with a barcode and the information identifying a specific filled vessel is the barcode.

* * * * *